US006992221B2

(12) United States Patent
Goudar

(10) Patent No.: US 6,992,221 B2
(45) Date of Patent: Jan. 31, 2006

(54) PROCESS TO PREPARE ARYLTRIAZOLINONES AND NOVEL INTERMEDIATES THERETO

(75) Inventor: Jaidev S. Goudar, Plainsboro, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 10/341,012

(22) Filed: Jan. 13, 2003

(65) Prior Publication Data

US 2003/0144528 A1 Jul. 31, 2003

Related U.S. Application Data

(62) Division of application No. 10/246,571, filed on Sep. 18, 2002, now Pat. No. 6,600,049, which is a division of application No. 09/663,336, filed on Sep. 18, 2000, now Pat. No. 6,492,527.

(60) Provisional application No. 60/159,247, filed on Oct. 13, 1999.

(51) Int. Cl.
    C07C 243/18    (2006.01)
    C07C 243/22    (2006.01)

(52) U.S. Cl. ....................................... 564/251

(58) Field of Classification Search ................ 564/251, 564/256

See application file for complete search history.

(56) References Cited

U.S. PATENT DOCUMENTS

| 3,786,094 A | 1/1974 | Girault et al. |
| 3,819,703 A | 6/1974 | Hammann et al. |
| 3,870,505 A | 3/1975 | Kaugars |
| 3,935,315 A | * 1/1976 | Boesch ................ 514/639 |
| 4,220,789 A | 9/1980 | Gozzo et al. |
| 4,400,517 A | 8/1983 | Gozzo et al. |
| 4,743,291 A | 5/1988 | Maravetz |
| 4,818,275 A | 4/1989 | Theodoridis |
| 4,980,480 A | 12/1990 | Theodoridis et al. |
| 5,125,958 A | 6/1992 | Poss |
| 5,130,310 A | 7/1992 | Weidman et al. |
| 5,376,670 A | 12/1994 | Connor et al. |
| 5,440,045 A | 8/1995 | Bailey et al. |
| 5,449,784 A | 9/1995 | Goudar |
| 5,543,541 A | 8/1996 | Goudar |
| 5,723,624 A | 3/1998 | Stolz-Dunn |
| 6,258,957 B1 | 7/2001 | Linker |

FOREIGN PATENT DOCUMENTS

| DE | 24 36 544 | 4/1975 |
| EP | 0 371 438 | 6/1990 |
| GB | 1603407 | 11/1981 |
| JP | 02 091062 A | 3/1990 |
| WO | WO 86 02642 A | 5/1986 |

OTHER PUBLICATIONS

Database CAPLUS on STN, Acc. No. 1978:579912, Kheruze et al., Zhurnal Organicheskoi Khimii (1978), 14(7), p. 1396–140 (abstract).*
Database CAPLUS on STN, Acc. No. 1938:44890, Justoni, Gazzetta Chimica Italiana (1938), 68, p. 49–59 (abstract).*
Database CAPLUS on STN, Acc. No. 1977:43613, Shawali et al., J. Heterocyclic Chemistry (1976), 13(5), p. 1137–40 (abstract).*
Database CAPLUS on STN, Acc. No. 1985:402045, Bernard et al., Farmaco, Edizione Scientifica (1985), 40(4), p. 259–71 (abstract).*
Sharp, L.B., "Derivatives of 1,2,4–Triazole and Pyrazole," JACS.,68, 588 (1946).
Shawali, A. S., et al., "Hydrazidoyl Halides in the Synthesis of Heterocycles," J. Het. Chem., 17, 833 (1980).
Tanaka, K., et al., "Synthesis of Trifluoromethyltriazoles from Trifluoroacetohydrazonoyl Bromides," J. Het. Chem., 24, 1391 (1987).

(Continued)

*Primary Examiner*—Brian Davis
(74) *Attorney, Agent, or Firm*—FMC Corporation

(57) ABSTRACT

A process is described for preparing 1-aryltriazolinones of formula I useful in the production of commercial herbicides:

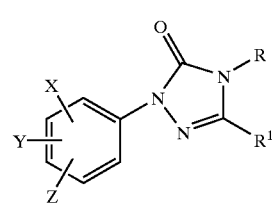

I by (i) carbonylating an amidrazone of formula (A) with one or more carbonylating agent, or by (ii) condensing a hydrazonoyl derivative of formula (A) with one or more ring-forming agent, wherein formula (A) is

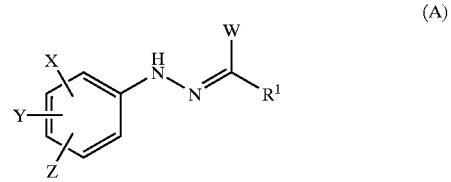

(A)

where W, X, Y, Z, and $R^1$ are fully described herein. Preferred are those where W is halogen or —NHR where R is hydrogen or haloalkyl; X and Y are independently selected from hydrogen, chloro, or fluoro; Z is hydrogen, bromo, iodo, nitro, amino, or methylsulfonylamino; and $R^1$ is methyl. Certain compounds of formula (A) are novel compositions of matter. The process as described herein has utility in providing compounds of formula I in unexpectedly high yield and purity.

1 Claim, No Drawings

OTHER PUBLICATIONS

Barnish, I.T., et al; J. Het. Chem., 23, 417 (1986).
Fusco, R., et al; Gazzetta Chemica Italiana, 68, 147–54 (1938).
N–Phenyl–Acetamidrazone, BRN 908013 (online database) Beilstein Informationssysteme Gmbh, Frankfurt, DE.
N–Phenyl–Butyramidrazone, BRN 4975360 (online database) and JOCS; 53(18), 4349–53 (1988).
2–(2–Chlorophenyl)hydrazidethanimidic acid (online database), Acession No. 119:159819; CAS, Colombus, OH.
N–Phenylethanecarbohydrazonyl chloride, BRN 7987320 (online database) and Australian JOC., 51(6), 499–510 (1988).
N–Phenylpropanehydrazonoyl chloride, BRN 5500936 (online database) and Chem. Pharm. Bull., 36(2),800–02 (1988).
N –(2,4–Dichlorophenyl)acetohydrazonoyl chloride, BRN 3270077 (online database) and Justus Liebigs Annalen Der Chemie, 591, 200–30(1955).
Cram & Hammond, "Organic Chemistry", McGraw Hill Book Co., N.Y. (1964) 2nd edition, pp. 565–567.
International Search Report for PCT/US00/28240 of Dec. 10, 2000.

* cited by examiner

PROCESS TO PREPARE ARYLTRIAZOLINONES AND NOVEL INTERMEDIATES THERETO

This application is a Divisional Application of prior U.S. patent application Ser. No. 10/246,571, filed Sep. 18, 2002; now U.S. Pat. No. 6,600,049 which is a Divisional Application of U.S. patent application Ser. No. 09/663,336, filed Sep. 18, 2000, now U.S. Pat. No. 6,492,527; which claims the benefit of U.S. Provisional Application No. 60/159,247, filed Oct. 13, 1999.

The present invention relates generally to the field of process chemistry as used in the preparation of commercially valuable chemical products. In particular, it pertains to processes related to 1-aryltriazolinone ring formation and to novel intermediates useful in these processes.

The compound 4,5-dihydro-3-methyl-1-phenyl-1,2,4-triazol-5(1H)-one, among others, is a particularly useful 1-aryltriazolinone critical in the manufacture of commercially important herbicides. For example, U.S. Pat. Nos. 4,818,275 and 5,125,958 fully describe conversions of 1-aryltriazolinone intermediates to known herbicides.

Some known methods for the preparation of 1-aryltriazolinones require formation of a 1-aryltriazolidinone ring followed by conversion of the 1-aryltriazolidinone ring to the desired 1-aryltriazolinone. This requirement is disadvantageous because it adds an additional step to the process of preparing 1-aryltriazolinones. Other known methods provide less than optimum yields of 1-aryltriazolinone because of by-product formation. Given the commercial value of 1-aryltriazolinones, improved processes for their preparation are therefore needed.

SUMMARY OF THE INVENTION

It has now been found that commercially useful 1-aryltriazolinones of formula I

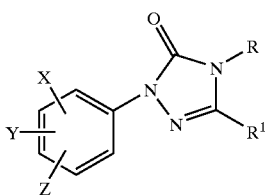

I can be prepared in excellent yield and purity by (i) carbonylating an amidrazone of formula (A) with at least one carbonylating agent, or by (ii) condensing a hydrazonoyl derivative of formula (A) with at least one ring-forming agent, wherein formula (A) is

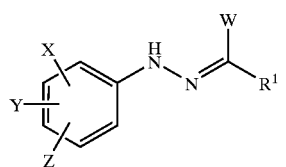

(A)

where W, X, Y, Z, and $R^1$ are fully described below. Preferred are those where W is halogen or —NHR where R is hydrogen or haloalkyl; X and Y are independently selected from hydrogen, chloro, or fluoro; Z is hydrogen, bromo, iodo, nitro, amino, or methylsulfonylamino; and $R^1$ is methyl. Additionally, certain compounds of formula (A) used to prepare 1-aryltriazolinones of formula I are also novel and are included among the preferred embodiments of the present invention. These and other features, aspects, and advantages of the present invention will become better understood with reference to the following description and appended claims.

DEFINITIONS

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated the substituent terms "alkyl", "alkoxy", and "haloalkyl", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "aryl" refers to phenyl or naphthyl optionally substituted with one or more halogen, alkyl, alkoxy, or haloalkyl. "Halogen" or "halo" refers to fluorine, bromine, iodine, or chlorine. The term "ambient temperature" refers to a temperature in the range of about 20° C. to about 30° C. Certain solvents, catalysts, and the like are known by their acronyms. These include the acronyms "DMAC" meaning N,N-dimethelyacetamide, "DMF" meaning N,N-dimethylformamide, "THF" meaning tetrahydrofuran, "DMAP" meaning 4-dimethylaminopyridine, "DBN" meaning 1,5-diazabicyclo[4.3.0]non-5-ene, and "DBU" meaning 1,8-diazabicyclo[5.4.0]undec-7-ene. The term "glymes" refers to a class of solvents comprised of monoglyme, diglyme, triglyme, tetraglyme, and polyglyme. The term "GC" refers to gas chromatography or gas chromatographic methods of analyses.

The term "amidrazone" or "amidrazone of formula (A)" is synonymous with and refers to a 2-(optionally-substituted phenyl)hydrazidethaneimidic acid, for example, but not limited to 2-(2,4-dichlorophenyl)hydrazidethaneimidic acid. The term "hydrazonoyl derivative" or "hydrazonoyl derivative of formula (A)" is synonymous with and refers to a N-(optionally-substituted phenyl)ethanehydrazonoyl derivative, for example, but not limited to N-(2,4-dichlorophyenyl)enthanehydrazonoyl chloride. The term "compound or compounds of formula (A)" refers to both amidrazone and hydrazonoyl derivatives. The term "compound or compounds of formula I" is synonymous with and refers to 1-aryltriazolinone(s), for example, but not limited to 4,5-dihydro-1-(2,4-dichlorophenyl)-3-methyl-1,2,4-triazol-5(1H)-one.

DETAILED DESCRIPTION OF THE INVENTION

One embodiment of the present invention relates to a process for preparing a compound of formula I:

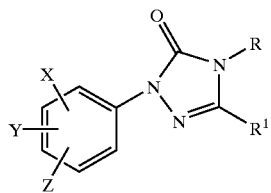

I wherein an amidrazone of formula (A) is carbonylated with at least one carbonylating agent, where formula (A) is:

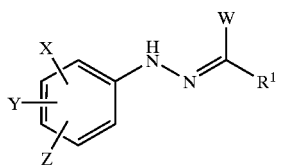

(A)

and wherein X and Y are independently selected from hydrogen, halogen, nitro, and amino; Z is selected from hydrogen, halogen, alkyl, alkoxy, nitro, amino, or alkylsulfonylamino; W is —NHR where R is hydrogen, alkyl, or haloalkyl; and, $R^1$ is hydrogen, alkyl, haloalkyl, alkoxy, acetyl, or aryl.

Preferred species of amidrazone (A) with which to conduct the carbonylation reaction of the present invention are selected from those wherein X and Y are independently selected from hydrogen, chloro, or fluoro; Z is hydrogen, bromo, iodo, nitro, amino, or methylsulfonylamino; R is hydrogen or difluoromethyl; and $R^1$ is $C_1$ to $C_{12}$ alkyl.

More preferred species of amidrazone (A) are selected from those wherein X, Y, and R are hydrogen, Z is hydrogen, 5-nitro, or 5-amino, and $R^1$ is methyl, ethyl, or propyl; wherein X and R are hydrogen, Y is 4-chloro, Z is hydrogen or 5-nitro, and $R^1$ is methyl, ethyl, or propyl; wherein X is 2-chloro or 2-fluoro, Y, Z, and R are hydrogen, and $R^1$ is methyl, ethyl, or propyl; or wherein X is 2-chloro or 2-fluoro, Y is 4-chloro, Z is hydrogen, 5-bromo, 5-iodo, or 5-nitro, R is hydrogen, and $R^1$ is methyl, ethyl, or propyl.

Most preferred species of amidrazone (A) are selected from those wherein X, Y, Z and R are hydrogen, and $R^1$ is methyl; or wherein X is 2-fluoro, Y is 4-chloro, Z and R are hydrogen, and $R^1$ is methyl.

For conducting the carbonylation of amidrazone (A), the use of at least one suitable organic solvent is preferably employed.

Preferred organic solvents, both polar and a polar, useful in the process of the present invention include halogenated solvents, for example, such as, without limitation, chlorobenzene, carbon tetrachloride, bromodichloromethane, dibromochloromethane, bromoform, chloroform, bromochloromethane, butyl chloride, dichloromethane, tetrachloroethylene, trichloroethylene, 1,1,1-trichloroethane, 1,1,2-trichloroethane, 1,1-dichloroetane, 2-chloropropane, hexafluorobenzene, 1,2,4-trichlorobenzene, 1-2-dichlorobenzene, fluorobenzene and other halogenated solvents known in the art.

Preferred polar organic solvents include ethers, for example, such as, without limitation, dimethoxymethane, THF, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, tert.-butyl ethyl ether, tert.-butyl methyl ether and other ether solvents known in the art. Other polar organic solvents useful in the context of the present invention include, for example, without limitation, propionitrile, ethyl formate, methyl acetate, hexachloroacetone, acetone, ethyl methyl ketone, ethyl acetate, nitromethane, nitrobenzene, glymes, and other polar solvents known in the art.

Other organic solvents useful herein include polar aprotic solvents, for example, such as, without limitation, DMF, DMAC, 1,3-dimethyl-3,4,5,6-tetrahydro-2(1H)-pyrimidinone, 1,3-dimethyl-2-imidazolidinone, N-methylpyrrolidinone, formamide, N-methylacetamide, N-methylformamide, acetonitrile, dimethyl sulfoxide, sulfolane, N,N-dimethylpropionamide, tetramethylurea, hexamethylphosphoramide and other polar aprotic solvents known in the art.

Yet other organic solvents useful for implementation of the present invention include protic solvents, for example, such as, without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutanol, tert.-butanol, 2-ethoxyethanol, diethylene glycol, 1-, 2-, or 3-pentanol, 2,2-dimethyl-1-propanol, tert.-pentanol, cyclohexanol, anisole, benzyl alcohol, glycerol and other protic solvents known in the art.

Further organic solvents useful in the present invention include: acidic solvents, for example, such as, without limitation, trifluoroacetic acid, acetic acid, formic acid and other acidic solvents known in the art; basic solvents, for example, such as, without limitation, 2-, 3-, or 4-picoline, pyrrole, pyrrolidine, morpholine, pyridine, piperidine, triethylamine and other basic solvents known in the art; and hydrocarbon solvents, for example, such as, without limitation, benzene, cyclohexane, pentane, hexane, toluene, cycloheptane, methylcyclohexane, heptane, ethylbenzene, ortho-, meta-, or para-xylene, octane, indane, nonane, naphthaline and other hydrocarbon solvents known in the art.

Organic solvents most suitable for conducting the carbonylation of amidrazone (A) are those that are low cost, best enhance the solubility of the starting materials to promote rate of reaction, and offer minimum solvent decomposition. Accordingly, preferred organic solvents include DMF, DMAC, acetonitrile, toluene, THF, and glymes. More preferred solvents include acetonitrile, toluene, tetrahydrofuran, monoglyme, and diglyme. The most preferred organic solvent in which to conduct the carbonylation of amidrazone (A) is toluene.

In the course of conducting chemical reactions, especially large scale organic chemical reactions yielding commercial quantities of desired product, a balance must be met between having to handle too much solvent and yet provide sufficient solvent to afford optimum reaction conditions. A useful ratio of solvent to amidrazone (A) to afford optimum reaction conditions is in the range of about 2.5/1 to about 20/1 wt/wt, preferably about 3/1 to about 15/1.

In order to form a compound of formula I, an amidrazone of formula (A) is carbonylated with at least one carbony lating agent. Useful carbonylating agents are represented by the following formula:

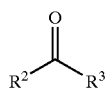

wherein $R^2$ and $R^3$ are the same and are selected from the group consisting of halogen, alkoxy, dichloromethoxy, trichloromethoxy, imidazol-1-yl, 2-methylimidazol-1-yl, phenoxy or naphthoxy wherein phenoxy and naphthoxy are optionally substituted with halogen, alkoxy, or nitro; or wherein $R^2$ and $R^3$ are different where, for example, $R^2$ is halo, and $R^3$ is alkoxy; provided that if the carbonylating agent is selected wherein $R^2$ and $R^3$ are chloro, at least one other carbonylating agent is also selected. Preferred carbonylating agents are those wherein $R^2$ and $R^3$ are the same and are selected from the group consisting of dichloromethoxy, trichloromethoxy, imidazol-1-yl, or phenoxy optionally substituted with halogen, alkoxy, or nitro. A more preferred carbonylating agent with which to carbonylate amidrazone (A) is that wherein $R^2$ and $R^3$ are each phenoxy. A preferred mole ratio of carbonylating agent to amidrazone (A) is in the range of about 1/1 to about 2.5/1, more preferably about 1.1/1 to about 1.5/1.

Preferably, the carbonylation of an amidrazone of formula (A) to form a compound of formula I is conducted in the presence of an acid or base catalyst. The catalyst need not be present in order to form a compound of formula I; however, its presence will generally accelerate the formation of a compound of formula I. Whether or not a catalyst is preferably present may depend upon the compound of formula I being formed, the amidrazone (A) being used as the reactant, the catalyst, the desired reaction time, and the reaction temperature, which one of ordinary skill in the art can readily determine based on general knowledge and this disclosure.

An acid catalyst useful in the context of the present invention can be a protic (Brontsted) acid or an electron pair-accepting (Lewis) acid. Acid catalysts include, for example, mineral, organic, inorganic, and organometallic acids. Preferred acid catalysts include, but are not limited to, hydrochloric acid, hydrobromic acid, hydroiodic acid, sulfuric acid, perchloric acid, acetic acid, trifluoroacetic acid, trifluoromethanesulfonic acid, chlorosulfonic acid, methanesulfonic acid, para-toluenesulfonic acid, camphorsulfonic acid, benzenesulfonic acid, boron trifluoride, boron trifluoride etherate, aluminium chloride, zinc chloride, and lanthanum series trifluoromethanesulfonates such as the trifluoromethanesulfonates of scandium, praseodymium, and ytterbium, and other acid catalysts known in the art.

Preferred acid catalysts for use in carbonylating an amidrazone of formula (A) include, but are not limited to, boron trifluoride, aluminum chloride, lanthanum series trifluoromethanesulfonates, methanesulfonic acid, para-touluenesulfonic acid, acetic acid, and trifluoroacetic acid. Particularly preferred acid catalysts include boron trifluoride, scandium trifluoromethadesulfonate, methanesulfonic acid, and para-touluenesulfonic acid.

Preferably, the acid catalyst is present in a mole ratio of acid catalyst to amidrazone (A) in a range of about 0.0001/1 to about 1/1, preferably in a range of about 0.001/1 to about 0.1/1. Additional amounts of acid catalyst can be added if necessary to drive the reaction faster, for example.

Preferred base catalysts include, but are not limited to, alkali metal, alkaline earth metal, and transition metal halides, hydrides, hydroxides, bicarbonates, carbonates, and the like. Metal halides useful in the present context include, but are not limited to, lithium chloride, lithium fluoride, lithium bromide, lithium iodide, sodium chloride, sodium fluoride, sodium bromide, sodium iodide, potassium chloride, potassium fluoride, potassium bromide, potassium iodide, magnesium chloride, magnesium fluoride, magnesium bromide, magnesium iodide, calcium chloride, calcium fluoride, calcium bromide, calcium iodide, silver bromide, and silver iodide. Metal hydrides useful in the present context include, but are not limited to, lithium hydride, sodium hydride, potassium hydride, magnesium hydride, calcium hydride, and barium hydride. Metal hydroxides useful in the present context include, but are not limited to, lithium hydroxide, sodium hydroxide, potassium hydroxide, magnesium hydroxide, calcium hydroxide, and barium hydroxide. Metal bicarbonates useful in the present context include, but are not limited to, sodium bicarbonate, and potassium bicarbonate. Metal carbonates useful in the present context include, but are not limited to, sodium carbonate and potassium carbonate. One of ordinary skill, upon receipt of the teachings hereof, may select other alkali metal, alkaline earth metal, and transition metal halides, hydrides, hydroxides, bicarbonates, and carbonates known in the art as catalysts.

Useful base catalysts also include alkali metal alkoxides, such as, without limitation, sodium methoxide, sodium ethoxide, potassium methoxide, potassium ethoxide, potassium tert.-butoxide, and other alkali metal alkoxides known in the art. Other useful base catalysts include organic alkyl amines and cyclic amines, for example, but are not limited to methylamine, ethylamine, dimethylamine, diethylamine, trimethylamine, triethylamine, ethyldiisopropylamine, butylamine, pyridine, DMAP, 2,6-dimethylpyridine, piperidine, piperazine, morpholine, quinoline, DBN, DBU, and other alkyl amines and cyclic amines known in the art.

Preferred base catalysts for use in carbonylating an amidrazone of formula (A) include sodium carbonate, potassium carbonate, sodium hydride, triethylamine, pyridine, DMAP, DBN, DBU, sodium methoxide, potassium methoxide, and potassium tert-butoxide. Particularly preferred base catalysts include sodium carbonate, potassium carbonate, DMAP, DBN, and DBU.

The base catalyst used in the present invention can be present in a mole ratio of base catalyst to amidrazone (A) in a range of about 0.0001/1 to about 1/1, preferably in a range of about 0.001/1 to about 0.1/1. Additional amounts of base catalyst may be added if necessary to drive the reaction faster, for example.

The temperature at which and the period for which a chemical reaction such as the carbonylation of amidrazone (A) is conducted will vary according to, among other things, the solvent or solvents in which the reaction is conducted, the reaction format (e.g., batch, semi-batch, or continuous), the carbonylating agent, and/or the formula of amidrazone (A), and whether or not a catalyst is used. The carbonylation of amidrazone (A) as set forth herein is generally conducted at a temperature in the range of about 10° C. to about 200° C. for a period of time of up to about 20 hours, preferably in the range of about ambient temperature to about 160° C. for about 10 hours, and more preferably up to about 5 hours.

Generally, in a process of carbonylating an amidrazone (A), a hydrazine derivative, for example, 2,4-dichlorophenylhydrazine (1) is first prepared from its hydrochloride salt by treating the salt with a base, such as aqueous sodium hydroxide, giving the free hydrazine (1). The free hydrazine (1) is in turn reacted with, for example, ethyl acetimidate at a temperature of about 0° C. to about ambient temperature in an appropriate solvent such as methylene chloride, yielding the corresponding amidrazone (A), 2,4-dichlorophenylhydrazidethaneimidic acid. Amidrazone (A) is in turn carbonylated with, for example, diphenyl carbonate at a temperature of about 100° C. to about 115° C. in a appropriate solvent such as toluene, yielding the corresponding compound of formula (I), 45-dihydro-1-(2,4-dichlorophenyl)-3-methyl-1,2,4-triazol-5(1H)-one. The carbonylation of amidrazone (A) to the compound of formula (I) is routinely aided with a catalyst, such as DMAP. A detailed procedure for the preparation, and carbonylation of an amidrazone (A) to yield a compound of formula (I) is set forth in Example 3 hereinbelow.

In a second embodiment of the present invention, the process for preparing a compound of formula (I):

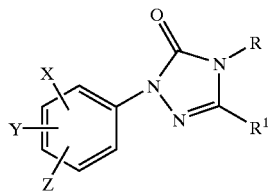

I involves a condensation reaction of a hydrazonoyl derivative of formula (A) with at least one ring-forming agent, where formula (A) is:

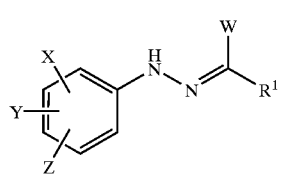

(A)

and wherein X and Y are independently selected from hydrogen, halogen, nitro, and amino; Z is selected from hydrogen, halogen, alkyl, alkoxy, nitro, amino, or alkylsulfonylamino; W is halogen, —NCO, —OSO$_2$CH$_3$, —OSO$_2$CF$_3$, or —OSO$_2$(p-CH$_3$Ph); and R$^1$ is hydrogen, alkyl, haloalkyl, alkoxy, acetyl, or aryl.

Preferred species of hydrazonoyl derivative (A) with which to conduct the condensation reaction of the present invention are selected from those wherein W is halogen; X and Y are independently selected from hydrogen, chloro, or fluoro; Z is hydrogen, bromo, iodo, nitro, amino, or methylsulfonylamino; and R$^1$ is C$_1$ to C$_{12}$ alkyl.

More preferred species of hydrazonoyl derivative (A) are selected from those wherein W is chloro; X and Y are hydrogen; Z is hydrogen, 5-nitro, or 5-amino; and R$^1$ is methyl, ethyl, or propyl; wherein W is chloro; X is hydrogen; Y is 4-chloro; Z is hydrogen or 5-nitro; and R$^1$ is methyl, ethyl, or propyl; wherein W is chloro; X is 2-chloro or 2-fluoro; Y and Z are hydrogen; and R$^1$ is methyl, ethyl, or propyl; or wherein W is chloro; X is 2-chloro or 2-fluoro, Y is 4-chloro; Z is hydrogen 5-bromo, 5-iodo, or 5-nitro; and R$^1$ is methyl, ethyl, or propyl.

Most preferred species of hydrazonoyl derivative (A) are selected from those wherein W is chloro; X, Y, and Z are hydrogen; and R$^1$ is methyl, or wherein W is chloro; X is 2-fluoro; Y is 4-chloro, Z is hydrogen, and R$^1$ is methyl.

For conducting the condensation reaction of a hydrazonoyl derivative of formula (A), at least one organic solvent, such as those described above, is preferably employed. Preferred organic solvents are those that are low cost, best enhance the solubility of the starting materials to promote rate of reaction, and offer minimum solvent decomposition. Accordingly, preferred organic solvents include glymes, DMF, DMAC, 1-methyl-2-pyrrolidinone, and methyl sulfoxide. More preferred solvents are glymes, DMF, and DMAC. Particularly preferred solvents are DMAC and diglyme. A useful ratio of solvent to hydrozonoyl derivative (A) to afford optimum reaction conditions is in the range of about 2.5/1 to about 20/1 wt/wt, preferably about 3/1 to about 15/1.

Accordingly, when diglyme is the solvent of choice in which to conduct the condensation reaction of a hydrazonoyl derivative of formula (A), the rate of reaction benefits from the inclusion of a reaction rate-promoting amount of water. Inasmuch as the reaction proceeds in an acceptable manner without the presence of water, it is believed that it aids in dissolving the ring-forming agent thereby enhancing its contact with hydrazonoyl derivative (A) causing the reaction to proceed at a faster rate. The ratio of reaction rate-promoting amount of water to solvent as used in the present invention is in the range of about 0.001/1 to about 1/1 wt/wt. A preferred ratio is about 0.01/1 to about 0.9/1, more preferably about 0.04/1 to about 0.8/1.

In order to form a compound of formula I, a hydrazonoyl derivative of formula (A) is condensed with at least one ring-forming agent. Useful ring-forming agents in the process of the present invention include, for example, such as, without limitation sodium cyanate, potassium cyanate, silver cyanate, methyl carbamate, ethyl carbamate, phenyl carbamate, cyanic acid, isocyanic acid, acetyl isocyanate, and trimethylsilyl isocyanate. Preferred ring-forming agents are sodium cyanate, potassium cyanate, cyanic acid, isocyanic acid, and phenyl carbamate. More preferred ring-forming agents are sodium cyanate and potassium cyanate, particularly potassium cyanate. A useful mole ratio of ring-forming agent to hydrazonoyl derivative (A) of about 1/1 to about 5/1, preferably about 1.05/1 to about 2/1, and more preferably about 1.1/1 to about 1.3/1.

Preferably, the condensation reaction of a hydrazonoyl derivative of formula (A) to form a compound of formula I is conducted in the presence of a catalyst. Accordingly, useful catalysts, such as those described above, for condensing hydrazonoyl derivative (A) include potassium iodide, potassium fluoride, silver bromide, silver iodide, and elemental iodine. Preferred catalysts are potassium iodide, potassium fluoride, and elemental iodine, particularly potassium fluoride. The catalyst used in the present invention can be present in a mole ratio of catalyst to hydrazonoyl derivative (A) in a range of about 0.001/1 to about 0.1/1, preferably about 0.004/1 to about 0.06/1. Additional amounts of catalyst may be added if necessary to drive the reaction faster, for example.

The temperature at which and the period for which a chemical reaction such as the condensation reaction of a hydrazonoyl derivative of formula (A) is conducted will vary, as discussed above. The condensing of hydrazonoyl derivative (A) as set forth herein is generally conducted at a temperature in the range of about −10° C. to about 160° C. for a period of time up to about 30 hours, preferably in the range of about 0° C. to about 100° C. for up to about 20 hours, more preferably up to about 20 hours.

Generally in a process of condensing a hydrazonoyl derivative of formula (A) to form a compound of formula (I), the free hydrazine (1) as described above, for example, 2,4-dichlorophenylhydrazine (1) is reacted with acetic anhydride at a temperature of about 10° C. in an appropriate solvent such as ethyl acetate, yielding the corresponding 1acetyl-2-(2,4-dichlorophenyl)hydrazine (2). The hydrazine (2) is then chlorinated with phosphorous oxychloride at a temperature of about 110° C. in an appropriate solvent such as toluene, yielding the hydrazonoyl derivative of formula (A), N-(2,4-dichlorophenyl)ethanehydrozonoyl chloride. The hydrozonoyl chloride (A) is condensed with a ring forming agent, for example, potassium cyanate at a temperature of about 40° C. to about 65° C. in an appropriate solvent such as DMAC, yielding the corresponding compound of formula (I), 45-dihydro-1-(2,4-dichlorophenyl)-3-methyl-1,2,4-triazol-5(1H)-one. The condensing of hydrozonoyl chloride (A) to the compound of formula (I) in solvents such as DMAC is routinely aided by the presence of a catalyst, such as potassium fluoride. A detailed procedure for the preparation, and the potassium fluoride-catalized condensing of the hydrozonoyl chloride (A) with the ring forming agent potassium cyanate in DMAC to yield a compound of formula (I) is set forth in Example 1 hereinbelow.

In a variation of the process of condensing a hydrazonoyl derivative of formula (A) to form a compound of formula (I), the hyrazonoyl derivative (A), for example, N-(2,4-dichlorophenyl)ethanehydrozonoyl chloride is conducted at ambient temperature in the solvent diglyme in the presence of a catalytic amount of water. A detailed procedure for the preparation, and the water-catalized condensing of the hydrozonoyl chloride (A) with the ring forming agent potassium cyanate in diglyme to yield a compound of formula (I) is set forth in Example 2 hereinbelow.

A third embodiment of the present invention relates to novel amidrazone and hydrazonoyl derivatives of formula (A) useful in the preparation of compounds of formula I. These compounds are represented-by formula (A):

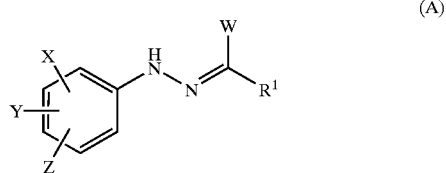

wherein;

W is halogen, —NCO, —OSO$_2$CH$_3$, —OSO$_2$CF$_3$, —OSO$_2$(p-CH$_3$Ph); or —NHR where R is hydrogen, alkyl, or haloalkyl; X and Y are independently selected from hydrogen, halogen, nitro, and amino; Z is selected from hydrogen, halogen, alkyl, alkoxy, nitro, amino, or alkylsulfonylamino; and, R$^1$ is hydrogen, alkyl, haloalkyl, alkoxy, acetyl, or aryl.

Preferred novel compounds of formula (A) are those wherein W is halogen or —NHR where R is hydrogen or difluoromethyl; X and Y are independently selected from hydrogen, chloro, or fluoro; Z is hydrogen, bromo, iodo, nitro, amino, or methylsulfonylamino; and R$^1$ is C$_1$ to C$_{12}$ alkyl.

More preferred novel compounds of formula (A) are those wherein W is chloro or —NHR where R is hydrogen; X and Y are hydrogen; Z is hydrogen, 5-nitro, or 5-amino; and R$^1$ is methyl, ethyl, or propyl; those wherein W is chloro or —NHR where R is hydrogen; X is hydrogen, Y is 4-chloro, Z is hydrogen or 5-nitro; and R$^1$ is methyl, ethyl, or propyl; those wherein W is chloro or —NHR where R is hydrogen; X is 2-chloro or 2-fluoro; Y and Z are hydrogen; and R$^1$ is methyl, ethyl, or propyl; and, those wherein W is chloro or —NHR where R is hydrogen; X is 2-chloro or 2-fluoro, Y is 4-chloro; Z is hydrogen, 5-bromo, 5-iodo, or 5-nitro; and R$^1$ is methyl, ethyl, or propyl.

Most preferred compounds of formula (A) are those wherein W is chloro or —NHR where R is hydrogen, X, Y, and Z are hydrogen, and R$^1$ is methyl; or wherein W is chloro or —NHR where R is hydrogen, X is 2-fluoro, Y is 4-chloro, Z is hydrogen, and R$^1$ is methyl.

The process of the present invention is carried out in accordance with the procedures shown in the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

This example illustrates a process for preparing 4,5-dihydro-1-(2,4-dichlorophenyl)-3-methyl-1,2,4-triazol-5 (1H)-one (I) from N-(2,4-dichlorophenyl) ethanehydrazonoyl chloride (A) in DMAC solvent A slurry of 101.4 grams (0.4751 mole) of 2,4-dichlorophenylhydrazine hydrochloride in 600 mL of water was stirred, and a solution of 20.9 grams (0.5225 mole) of sodium hydroxide in 100 mL of water was slowly added. During the addition, the reaction mixture thickened. An additional 50 mL of water was added. to aid fluidity. Upon completion of addition of the sodium hydroxide solution, an additional 70 mL of water was added. The reaction mixture was stirred for about 75 minutes, then it was extracted with three 300 mL portions of ethyl acetate. The extracts were combined and dried with magnesium sulfate. The mixture was filtered and the filtrate containing free 2,4-dichlorophenylhydrazine (1) was transferred to an appropriate reaction vessel. The stirred solution was cooled to about 10° C., and 58.2 grams (0.5701 mole) acetic anhydride was added dropwise. Upon completion of addition, gas chromatographic (GC) analysis of the reaction mixture indicated the reaction was about 99% complete. The cooling medium was removed, and a solution of 62.5 grams of potassium carbonate in 200 mL of water was added to the reaction mixture. The mixture was stirred for about five minutes and the organic layer was separated. The organic layer was concentrated under reduced pressure, yielding 102.0 grams (98% yield) of 1-acetyl-2-(2,4-dichlorophenyl)hydrazine (2).

A solution of 25.0 grams (0.1142 mole) of 1-acetyl-2-(2, 4-dichlorophenyl)hydrazine (2) in 120 grams of toluene was stirred, and 17.7 grams (0.1142 mole) of phosphorus oxychloride was added portionwise. Upon completion of addition the reaction mixture was warmed to about 110° C. where it stirred for about 30 minutes. GC analysis of the reaction mixture after this time indicated the reaction was complete. An additional 100 grams of toluene was added to the reaction mixture, and the solution was decanted into a separatory funnel. A residue in the reaction vessel was washed with about 40 grams of toluene, and the wash was also decanted into the separatory funnel. The toluene solution was then washed with an aqueous solution of 10% potassium carbonate. The aqueous layer was back-washed with two 75 gram portions of toluene. The combined toluene layer and washes was dried with magnesium sulfate. The mixture was filtered and the filtrate was concentrated under reduced pressure, yielding 21.3 grams (78.5% yield) of N-(2,4-dichlorophenyl)ethanehydrazonoyl chloride (A).

A solution of 21.3 grams (0.0896 mole) of N-(2,4-dichlorophenyl)ethanehydrazonoyl chloride (A) in 500 grams of N,N-dimethylacetamide (DMAC) was stirred and 9.1 grams (0.1127 mole) of potassium cyanate, followed by 0.1 gram (0.0018 mole) of potassium fluoride were added. Upon completion of addition, the heat of reaction caused the reaction mixture temperature to rise to about 60° C. The reaction mixture was stirred for 30 minutes during which time the reaction mixture temperature fell to about 45° C. GC analysis of the reaction mixture after this time indicated that the reaction was complete. The reaction mixture was concentrated under reduced pressure to a residue. The residue was slurried with about 100 grams of water, and the resultant solid was collected by filtration. The solid was washed with water and dried, yielding 21.2 grams of subject compound (I) (yield from (2) was 77.3%; yield from (A) was 96.8%).

EXAMPLE 2

This example illustrates a process for preparing 4,5-dihydro-1-(2,4-dichlorophenyl)-3-methyl-1,2,4-triazol-5 (1H)-one (I) from N-(2,4-dichlorophenyl) ethanehydrazonoyl chloride (A) in diglyme solvent A solution of 5.1 grams (0.0214 mole) of N-(2,4-dichlorophenyl)ethanehydrazonoyl chloride (A), prepared as in Example 1, 2.1 grams (0.0257 mole) potassium cyanate, and 3 mL of water in 51 mL of diglyme was stirred at ambient temperature for about 22 hours. After this time, the reaction mixture was concentrated under reduced pressure to a residue. The residue was dissolved in about 500 mL of ethyl acetate and washed with three 25 mL portions of water. The organic layer was dried with magnesium sulfate and filtered. The filtrate was concentrated under reduced pressure to a residue. The residue was triturated with hexane and the resultant solid was collected by filtration. The solid was dried, yielding 4.5 grams (85.2% yield from (A)) of subject compound (I).

EXAMPLE 3

This example illustrates a process for preparing 4,5-dihydro-1-(2,4-dichlorophenyl)-3-methyl-1,2,4-triazol-5 (1H)-one (I) from 2-(2,4-dichlorophenyl) hydrazidethaneimidic acid (A)

A stirred solution of 13.6 grams (0.1100 mole) of ethyl acetimidate hydrochloride and 13.2 grams (0.1300 mole) of triethylamine in 100 grams of methylene chloride was cooled to about 0° C. for five minutes, and 17.7 grams (0.1000 mole) of 2,4-dichlorophenylhydrazine (1) was added. Upon completion of addition the reaction mixture stirred at 0° C. for about one hour, then it was allowed to warm to ambient temperature where it stirred for about two hours. GC analysis of the reaction mixture indicated the presence of a small amount of unreacted (1). An additional 0.6 gram of ethyl acetimidate hydrochloride was added (total 14.2 gram—0.1150 mole), and the reaction mixture was stirred for an additional one hour. After this time the reaction mixture was washed with about 20 mL of water and dried with magnesium sulfate. The mixture was filtered, and the filtrate was concentrated under reduced pressure to a semi-solid residue. The residue was triturated with 20 mL of hexane, and the resultant solid was collected by filtration. The solid was washed with 50 mL of hexane and dried, yielding 20.4 grams (93.4% yield) of 2-(2,4-dichlorophenyl) hydrazidethaneimidic acid (A).

A stirred solution of 7.5 grams (0.0344 mole) of 2-(2,4-dichlorophenyl)hydrazidethaneimidic acid (A), 7.4 grams (0.0344 mole) of diphenyl carbonate, and 0.2 gram (0.0017 mole) of 4-dimethylaminopyridine (DMAP) in 20 grams of toluene was heated at reflux for about 30 minutes. GC analysis of the reaction mixture after this time indicated the presence of unreacted diphenyl carbonate. An additional 0.3 gram of (A) was added (total 7.8 grams—0.0358 mole), and the reaction mixture was heated at reflux for an additional 30 minutes. After this time the reaction mixture was cooled and concentrated under reduced pressure to a residue. The residue was slurried for about two hours in refluxing hexane, then it was collected by filtration, yielding about 8.1 grams of subject compound (I) (yield from (A) is 93.2%; yield from (1) is 87.0%).

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly this invention includes all modifications encompassed within the spirit and scope as defined by the following claims.

What is claimed is:
1. A compound of formula (A):

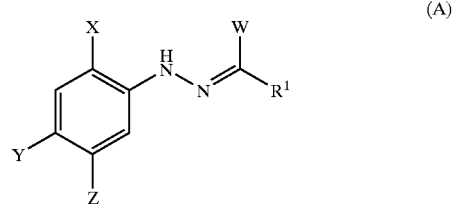

where X is fluoro, Y is chloro, Z is hydrogen, W is chloro and $R^1$ is selected from methyl or ethyl.

* * * * *